United States Patent [19]
Blake

[11] Patent Number: 6,124,132
[45] Date of Patent: Sep. 26, 2000

[54] USE OF ANTI-HIV IGA ANTIBODIES FOR PRODUCING IMMUNOLOGICAL PROTECTION AGAINST THE HUMAN IMMUNODEFICIENCY VIRUS

[75] Inventor: Milan Blake, New York, N.Y.

[73] Assignee: Blake Laboratories, Inc., New York, N.Y.

[*] Notice: This patent issued on a continued prosecution application filed under 37 CFR 1.53(d), and is subject to the twenty year patent term provisions of 35 U.S.C. 154(a)(2).

[21] Appl. No.: 08/916,063

[22] Filed: Aug. 21, 1997

Related U.S. Application Data

[63] Continuation of application No. 08/335,019, Nov. 7, 1994, abandoned.

[51] Int. Cl.$^7$ .............................. C12N 5/06; C12P 21/04; C12P 21/08; A61K 39/395
[52] U.S. Cl. .................. 435/339.1; 435/69.6; 435/70.21; 424/133.1; 424/142.1; 530/387.3
[58] Field of Search .............................. 424/133.1, 142.1; 435/69.6, 70.21, 339.1; 530/387.3

[56] References Cited

U.S. PATENT DOCUMENTS 5,258,177  11/1993  Uemura et al. ........................ 424/85.8

OTHER PUBLICATIONS

Duprat et al., Human immunodeficiency virus type 1 IgA antibody in breast milk and serum, Pediatr Infect Dis J, vol. 13, No. 7, pp. 603–608, especially Abstract, Methods, Mar. 1994.
Van De Perre et al., Infective and anti–infective properties of breastmilk from HIV–1–infected women., The Lancet, vol. 341, pp. 914–918, especially p. 914, Abstract, Apr. 1993.
Arendrop et al 1993 J. Gen. Virol 1993 vol. 74: 855–863
Faley et al 1992 Clin Exp. Immunol vol. 88: 1–5.
Fox Bio/Technology 1994 vol. 12:128 Kozlowski et al 1995 Advances in Moucosal Immunology 371 B: 1027–1030.
Burnett et al 1994 J. Immunol vol. 152: 4642.
Reichmann et al 1988 Nature vol. 332: 323–327 Queen et al. 1989 Pruc Natl. Acad. Ser. vol. 86: 10029–10033.
Chu, S.Y., J.W. Buehler, R.L. Berkelman (1990) "Impct of the Human Immunodeficiency Virus Epidemic on Mortality in Women of Reproductive Age, United States" JAMA 264(2):225–229.
Dimmock, N.J. (1984) "Mechanisms of Neutralization of Animal Viruses" J. Gen. Virol. 65:1015–1022.
Grimes, R.M., A.G. Randall, L.N. Nickey (1990) "Dealing with Aids in the '90s" Texas Medicine 86(11):36–37.
Halsey, J.F., B.H. Johnson, J.J. Cebra (1980) "Transport of Immunoglobulins from Serum into Colostrum" J. Exp. Med. 151:767–772.
Mazanec, M.B. et al. (1992) "Intracellular neutralization of virus by immunoglobulin A antibodies" Proc. Natl. Acad. Sci. USA 89:6901–6905.
McGhee, J.R. et al. (1992) "The mucosal immune system: from fundamental concepts to vaccine development" Vaccine 10(2):75–88.
Ogra, P.L., E.E. Leibovitz, G. Zhao–Ri (1989) "Oral Immunization and Secretory Immunity to Viruses" Current Topics in Microbiology and Immunology 146:73–81.
Takeda, A., C.U. Tuazon, F.A. Ennis (1988) "Antibody–Enhanced Infection by HIV–1 Via Fc Receptor–Mediated Entry" Science 242:580–583.
Taylor, H.P., N.J. Dimmick (1985) "Mechanism of Neutralization of Influenza Virus by Secretory IgA is Different from that of Monomeric IgA or IgG" J. Exp. Med. 161:198–209.
Wold, A.E. et al. (1990) "Secretory Immunoglobulin A Carries Oligosaccharide Receptors for *Escherichia coli* Type 1 Fimbrial Lectin" Infection and Immunity 58(9):3073–3077.

*Primary Examiner*—Hankyel Park
*Attorney, Agent, or Firm*—Saliwanchik, Lloyd & Saliwanchik

[57] ABSTRACT

The subject invention concerns the production and novel use of human anti-HIV IgA antibodies to confer passive immunity to HIV when administered in vivo to a subject. The IgA antibodies of the subject invention are selectively transported to and secreted in the mucosal tissue of the subject. The IgA antibodies can confer protection from HIV infection at locations within the body where HIV penetration usually occurs.

14 Claims, No Drawings

USE OF ANTI-HIV IGA ANTIBODIES FOR PRODUCING IMMUNOLOGICAL PROTECTION AGAINST THE HUMAN IMMUNODEFICIENCY VIRUS

This application is a continuation of application Ser. No. 08/335,019, filed Nov. 7, 1994 now abandoned.

FIELD OF THE INVENTION

The present invention concerns the field of immunity, antibodies, and vaccines. The present invention relates, in particular, to a method of using human antibodies or antibodies of mostly human structure of the immunoglobulin A isotype that are reactive with the Human Immunodeficiency Virus and which when administered to a person can neutralize the virus to prevent Acquired Immunodeficiency Disease.

BACKGROUND OF THE INVENTION

The Centers for Disease Control reported that within the U.S. alone 109,167 cases of Acquired Immunodeficiency Disease Syndrome (AIDS) have been diagnosed since 1981 and that approximately 40,000 persons are living with AIDS. These numbers, however, represent individuals who are currently showing the signs and symptoms of this progressive disease and not the estimated 1.5 million Americans who are infected by the Human Immunodeficiency Virus (HIV) (Grimes et al, 1990). Originally, the HIV infection/AIDS epidemic in the United States was confined to the homosexual population and intravenous drug users. However, the infection has now proceeded into the domain of the American family through heterosexual transmission and vertical transmission. In fact, from the latest figures, the population which has had the greatest increase in seropositivity for the virus has been women between the ages of 18–24 years of age (Sato et al, 1989). This move into the heterosexual population can also be seen in a recent study that assesses the effect of HIV on the mortality of women in the United States between 15 to 44 years of age. Between 1985 and 1988, the death rate for HIV/AIDS quadrupled (0.6 per 100,000 to 2.5 per 100,000), and by 1987, HIV/AIDS had become one of the 10 leading causes of death within this population. The majority of deaths in both black and white women occurred in women 25 to 35 years of age, for whom HIV-related deaths accounted for 11% and 3% of all deaths in 1988, respectively. If current mortality trends continue, HIV/AIDS can be expected to become one of the five leading causes of death in women of reproductive age by the mid 1990's. Because women infected with HIV are the major source of infection for infants, these trends in AIDS mortality in women forecast the impact of HIV on mortality in children as well (Chu et al, 1990).

With the exception of the intravenous drug use, the most common modality of transmission of HIV virus is by sexual activity. With this mode of transmission, the HIV virus' first contact with a naive individual is at the mucosal surface, be it the urogenital tract, gastrointestinal tract or the oral cavity. Once the virus comes in contact with these surfaces, it is thought that the virus enters the body through breaches in the epithelial surface such as small cuts or abrasions, or possibly directly through the epithelial cells. Directly underlying the epithelial cells is a space composed of loose network of connective tissue and lymph call the lamina propria containing the body's second line of defense to invading organisms. This fluid-filled space contains immunologically reactive cells in the form of macrophages, NK cells, Langerhans cells as well as T and B lymphocytes. In addition, the fluid from this space is continually being drained into regional lymph nodes containing more of these defensive cells. It is within the lamina propria that HIV first comes in contact with immune cells.

Like all viruses, the HIV viral particle only consists of genetic material enclosed in a protective capsule and relies totally on the machinery of other cells for replication and production of progeny. More specifically, the virus contains a protein on its surface which functions to bind the virus to a potential host cell. However, once bound, the virus proceeds through various means to get its genes into the host cell. Information contained within these nucleic acids instructs the host's cells biochemical equipment to preferentially process the viral information over that of the host cells' own products. Within the initial processing steps, viral proteins are made which in turn are responsible for reproducing numerous copies of the original viral genome. This greatly amplifies these specific nucleic acids over that contained in the original host cell. In turn, this newly synthesized genetic material, which is now in great abundance, increases the utilization of the host cell for production of the encapsulating material in which the viral genes are finally packaged and released to begin the infectious cycle once more. The virus' parasitic use of these host cells is quite abusive and depletes it of its energy and other necessary resources. Thus, such an infection is lethal for the host cell.

The CD4 antigen is the ligand used by the virus to enter human cells and begin the replication cycle which produces an endless cycle of more infective viral particles. In a non-infected host, the most abundant cells in the lamina propria which contain the CD4 antigen are the Langerhans cells. These cells are similar to macrophages in many respects but do not migrate from place to place as do macrophages. It is the Langerhans cells that are first to become infected and form the reservoir of shedding viruses which infect the remaining cells in the body that bear the CD4 antigen. However, because Langerhans cells are stationary, rarely do they enter the systemic system. Thus, for HIV viral particles to gain access to the blood, they must first infect other CD4-bearing cells which do migrate systemically. Most likely, these cells are lymphocytes in transit through the local lymphatic system. The shedding virus infect these cells and then through the natural trafficking mechanisms of the lymphocytes finally enter the blood stream. However, the course of these events occur over long periods of time ranging from days to months. This is the latency period which has recently been of such controversy. Early reports suggested that the HIV virus may remain dormant within cells for several months before proceeding to shed. However, current data give evidence that such a dormant period does not exist and the virus begins to shed immediately after infection.

Although the precise mechanisms of how immunoglobulins neutralize virus is not known, IgG, IgA and IgM antibodies have been described which are capable of neutralizing viral particles. Most of the vaccines directed at preventing HIV infections using either attenuated viral particles or recombinant HIV-1 envelope or core proteins have been administered intramuscularly or subcutaneously into individuals. This mode of vaccination is directed at humoral or systemic immune responses and elicits the production of IgG antibodies. This type of antibody remains primarily in the bloodstream of the individual in order to prevent blood-born disease. It has been suggested that some of these IgG antibodies that are reactive with the HIV virus may possibly enhance HIV-1 infection even though they had previously been shown to be neutralizing. It is thought that this enhancing effect occurs as a result of the IgG antibody acting as a bridge between the virus and the receptors for these immunoglobulins on antibody binding cells (Takeda et al, 1988).

IgA antibody is secreted by differentiated, activated lymphocytes in the lamina propria. The structure and function of IgA in accordance with the major objectives of mucosal immunity, is quite distinct from that of the IgG produced by the systemic immune system. For example, IgA antibodies reach the mucosa much faster and in greater abundance than that of IgG (Halsey, J. F. et al, 1980). The IgA on mucosal surfaces occurs predominantly in dimeric and tetrameric forms, having four to eight antigen-binding sites. Polymeric IgA has been shown to neutralize viruses more effectively than the monomer (Dimmock, 1993; Taylor et al, 1985). In addition, regions on IgA unrelated to the antigen-binding domains are recognized by the mucosal epithelium. This epithelium forms a boundary of cells between the lamina propria and the outside of the body. These cells will attach to areas on the IgA molecule, via receptors, and actively displace these antibodies from the lamina propria to the outside of the body. Thus these antibodies do not rely on mere diffusion to reach the mucosa in contrast to all the other types of antibodies produced in the body.

It is well known that virus-neutralizing antibodies occur at mucosal cell surfaces and are important in preventing local infection and disease (Ogra et al., 1989). The direct inhibitory effect of immunoglobulin A on the adherence of virus and bacteria to host mucosal epithelial cells has been documented in many experimental systems (Wold et al., 1990; Abraham et al., 1985). Both non-specific hydrophobic interactions as well as specific inhibition of binding between bacterial surface adhesions and complementary surface receptors on host epithelial cells are involved in this process (McGhee et al., 1992). It has also been shown that intracellular antibody-antigen reactions between IgA and viruses reduces the ability of virus to replicate (Mazanec et al., 1992).

Another rather unique feature of IgA antibody molecules is their rather extensive glycosylation. The sugar moieties covalently linked to IgA molecules is thought to reduce the proteolysis of the antibodies by proteases which are found in the digestive tract and other mucosal surfaces. Along with this glycosylation, another peptide is added to the IgA as it traffics through the epithelial cell. This peptide, know as the secretory piece or secretory component, further reduces the effects of any possible enzymatic digestion. Thus, the distinctive structure of the IgA molecule renders it resistant to degradation by enzymes and unusually prepared to reside in the milieu of the mucosa as compared with antibodies of other isotypes (e.g., IgG, IgM, etc.) that might be present in the body and on the mucosal surfaces.

Although the encounter of an IgA antibody with its corresponding antigen in the mucosa inhibits the absorption of the antigen to the epithelial cells, it does not result in the activation of the complement system and the generation of the cleavage products of the C3 and C5 components. It has been well documented that an encounter between an IgG antibody on the mucosal cell surface with its corresponding antigen, although inhibiting the absorption of the antigen to the mucosal cells, activates the complement system resulting in local tissue damage and an increased absorption of bystander antigens. Thus, it seems that one of the major biological roles of IgA at mucosal surfaces is the mitigation of the inflammatory side effects brought about by other immune effector mechanisms.

Passive immunity has been known since the science of Immunology began. This type of immunity differs from active immunity in that the immunoglobulins from one animal are transferred into another animal rather than using a vaccine or antigen to induce the animals' own cells to produce an antibody response. Early use of such techniques were used to cure numerous bacterial as well as viral infections. It was determined early on that if the immunoglobulin was produced in one species of animal and injected into a species of animal different from the first, a second injection of the same immunoglobulin preparation would yield devastating effects and most often result in the death of the recipient animal. However, if the antibodies of interest were produced in the same species as the recipient animal, such immunoglobulins could be administered repeatedly without ill effects. Such preparations are currently licensed and used for numerous different purposes. Gamma globulin received before a person travels abroad is one such preparation. The antibodies received within these passive vaccines are predominately IgG with only a minor concentration of IgA.

The most plentiful source of immunoglobulin A comes from lactating mothers in their breast milk. It has been demonstrated that this source of IgA protects the newborn from disease during the first months of life. This natural passive immunity from mother to child has been used since mammals began walking the earth.

It is an object of the subject invention to provide a method for protecting individuals from HIV infection through passive immunity using IgA antibodies to HIV at mucosal surfaces.

BRIEF SUMMARY OF THE INVENTION

The present invention relates, in particular, to a method of using human antibodies of the immunoglobulin A isotype that are reactive with the Human Immunodeficiency Virus (HIV). The materials and methods of the subject invention can neutralize the virus and prevent viral infection from occurring in vivo, thereby preventing Acquired Immunodeficiency Disease or delaying the onset of clinical symptoms. The IgA antibodies of the subject invention can be administered to a person, thereby conferring passive immunity to HIV through the presence of antibodies at mucosal surfaces throughout the body.

DETAILED DESCRIPTION OF THE INVENTION

The subject invention concerns a method for protecting an individual from infection with the human immunodeficiency virus (HIV). Specifically, IgA antibodies to HIV are administered to an individual to provide that person with a passive immunity to HIV infection. In a preferred embodiment, a source of anti-HIV IgA antibodies for passive immunity directed at the HIV virus would be from the breast milk of women who are seropositive for HIV antibody and had demonstrated that such antibody protected their newborn from HIV infection. Preferably, such IgA antibodies would be obtained from a pool of several different women infected with various strains of HIV. Thus, the purified antibodies would represent an antibody preparation capable of protecting a person from a wide variety of HIV strains and HIV mutants. The purified immunoglobulin A from such sources is fully assembled including the secretory piece which is added by the mother's secretory mammary glands. Such an antibody can be applied onto the mucosal surface directly but lacks the capability of returning to the mucosa if injected systemically. However, the secretory piece of these molecules can be chemically removed, thereby allowing the IgA antibody to be transported to the mucosa.

In another embodiment of the invention, IgA antibodies are produced through the creation of human hybridomas that produce antibody reactive with HIV. Methods for producing such hybridomas are known to those skilled in the art. The source of the initial human lymphocytes is preferably an individual who has been exposed to the HIV virus and was undergoing surgery for hysterectomy, appendectomy of tonsillectomy. All of these organs are a rich source of B lymphocytes secreting IgA antibody. The B lymphocytes are isolated using techniques that are specific for the tissue from which they are derived and immortalized using standard techniques for the production of human hybridomas. These hybridomas are then distributed into 96 well tissue culture plates containing the proper media and growth requirements. Thereafter, cell supernatants from the wells containing hybridomas are removed and tested not only for reactivity with either HIV virus particles or recombinant HIV proteins, but also for their ability to neutralize the virus and protect human CD4-bearing cells from infection. The hybridomas from wells containing such activity are removed, expanded and finally processed to obtain a single clone. The supernatants from the clone are retested using the same criteria to insure that the cloning process has been successful. The isotype of the secreted antibody is determined for each clone in order to identify those clones producing HIV-specific IgA antibody. These human hybridoma cells are then expanded and the antibody isolated and purified.

In a further embodiment, human B lymphocytes secreting IgA antibodies can be obtained using severe combined immunodeficiency mice having a human immune system (SCID-hu mice) reconstituted from human peripheral blood or fetal thymus, bone marrow, and lymph node. These mice can then be immunized with HIV viral particles or HIV encoded proteins including gp160, gp120, gp41 and peptide fragments thereof. After successive boosts with HIV antigen the human B lymphocytes can be rescued using Epstein Bar virus (EBV) transformation or phage library repertoires.

In an alternative embodiment, anti-HIV monoclonal IgA antibodies of the subject invention can be "humanized" through genetic engineering techniques known to those of ordinary skill in the art. Specifically, monoclonal antibodies to HIV are prepared by first immunizing an appropriate animal, such as a mouse, with HIV viral particles or HIV proteins. Hybridomas are then produced and screened for the production of HIV-reactive IgA antibodies using standard techniques. After selecting high-affinity anti-HIV IgA antibody-producing clones that are capable of neutralizing HIV, the cells are genetically engineered so that the variable region of the non-human antibody is joined to the constant regions from a human IgA antibody to form a chimeric antibody. In a related procedure, the hypervariable regions from a non-human antibody combining site derived from an anti-HIV antibody can be "grafted" onto framework regions of human IgA antibody. This latter technique, known as complementarity-determining region (CDR) grafting, provides for the production of a humanized IgA antibody having a pre-selected non-human antibody binding site specific for a given epitope on an antigen.

The IgA antibodies prepared according to the subject invention are then purified for use in humans. If the antibody has the secretory piece still attached, then it may optionally be removed prior to administering the antibody to the subject. The administration of the IgA antibodies may be according to any suitable method known in the art. For example, the antibodies can be injected intramuscularly or intravenously. The invention contemplates the administration of antibodies reactive to a single epitope or to multiple epitopes present on HIV viral particles or proteins. Further, the antibodies used according to the subject invention may consist of monoclonal, polyclonal or a mixture of monoclonal and/or polyclonal antibodies. The antibodies may comprise whole antibody or fragments thereof, such as $F(ab)_2$ Fab, etc. The antibodies can be administered in physiologically acceptable formulations that will minimize the immune response of the recipient to the antibodies.

It is expected that additional administrations of the anti-HIV IgA antibodies will be required over time as mucosal antibody titer decreases in an individual. Dosage levels of the anti-HIV IgA antibody to be administered, as well as appropriate formulations of the antibody preparation, can be readily determined by a person of ordinary skill in the art.

The antibodies of the subject invention can be used to protect uninfected people, particularly people at risk for infection with HIV, such as medical care providers. Moreover, the antibodies of the subject invention are also contemplated for use in assays for HIV, or for use as molecular weight standards, or as an inert protein in an assay.

It should be understood that the embodiments described herein are for illustrative purposes only and that various modifications or changes in light thereof will be suggested to persons skilled in the art and are to be included within the spirit and purview of this application and the scope of the appended claims.

REFERENCES

Grimes, R. M., A. G. Randall, and L. N. Nickey (1990) "Commentary. Dealing with AIDS in the '90s," *Tex. Med.* 86:36–37.

Sato, P. A., J. Chin, and J. M. Mann (1989) "Review of AIDS and HIV Infection: global epidemiology and statistics," *AIDS* 3 Suppl. 1:S301–S307.

Chu, S. Y., S. W. Buehler, and R. L. Berkelman (1990) "Impact of the human immunodeficiency virus epidemic on mortality in women of reproductive age, United States," *JAMA* 264:225–229.

Takeda, A., C. U. Tuazon, and F. A. Ennis (1988) "Antibody-enhanced infection by HIV-1 via Fc receptor-mediated entry," *Science* 242:580–583.

Halsey, J. F., B. H. Johnson, and J. J. Cebra (1980) "Transport of immunoglobulins from serum into colostrum," *J. Exp. Med.* 151:767–772.

Dimmock, N. J. (1993) "Mechanisms of neutralization of animal viruses,"*J. Gen. Virol.* 65:1015–1021.

Taylor, H. P., and N. J. Dimmock (1985) "Mechanism of neutralization of influenza virus by secretory IgA is different from that of monomeric IgA or IgG,"*J. Exp. Med.* 161:198–209.

Ogra, P. L., E. E. Leibovits, and G. Zhao-Ri (1989) "Oral immunization and secretory immunity to viruses," *Curr. Top. Microbiol. Immunol.* 146:73–82.

Wold, A. E., J. Mestecky, M. Tomana, et al. (1990) "Secretory immunoglobulin A carries oligosaccharide receptors for *Escherichia coli* type 1 fimbrial lectin," *Infect. Immun.* 58:3073–3077.

Abraham, S. N., E. H. Beachey (1985) "Host defenses against adhesion of bacteria to mucosal surfaces," J. F. Gallin and A. S. Fauci [eds.], *Advances in Host Defense Mechanisms,* Raven Press, New York, pp. 63–72.

McGhee, J. R., J. Mestecky, M. T. Dertzbaugh, J. H. Eldridge, M. Hirasawa, and H. Kiyono (1992) "The mucosal immune system: From fundamental concepts to vaccine development," *Vaccine* 10:75–88.

Mazanec, M. B., C. S. Kaetzel, M. E. Lamm, D. Fletcher, and J. G. Nedrud (1992) "Intracellular neutralization of virus by immunoglobulin A antibodies," *Proc. Natl. Acad. Sci. USA* 89:6901–6905.

What is claimed is:

1. A purified IgA antibody composition that is immunoreactive with human immunodeficiency virus, wherein said antibody composition consists essentially of secretory $IgA_1$ and $IgA_2$ isotypes.

2. The antibody composition according to claim 1, wherein said IgA antibody is obtained from breast milk pooled from a plurality of HIV-infected females.

3. A method for providing passive immunity to infection by the human immunodeficiency virus (HIV) in an animal susceptible to infection by HIV, said method comprising administering to said animal an IgA antibody composition that neutralizes HIV, wherein said IgA antibody composition consists essentially of secretory $IgA_1$ and $IgA_2$ isotypes.

4. The method, according to claim 3, wherein said IgA antibody composition is polyclonal.

5. The method, according to claim 3, wherein said IgA antibody composition is monoclonal.

6. The method, according to claim 3, wherein said IgA antibody composition comprises a mixture of polyclonal and monoclonal antibodies.

7. The method, according to claim 3, wherein said IgA antibody composition neutralizes HIV selected from the group consisting of HIV-1 and HIV-2.

8. The method, according to claim 4, wherein said polyclonal IgA antibody composition is obtained from the breast milk of HIV-infected females.

9. The method, according to claim 5, wherein said monoclonal IgA comprises a chimeric antibody wherein a non-human variable region with binding specificity to an HIV antigen is joined to human IgA constant regions.

10. The method, according to claim 5, wherein said monoclonal IgA comprises a non-human CDR operably linked to a human antibody framework region, wherein said CDR has binding specificity to an HIV antigen.

11. The method, according to claim 3, wherein said IgA antibody composition is treated to remove the secretory piece prior to administration to said animal.

12. The method, according to claim 4, wherein said polyclonal IgA antibody composition is obtained from breast milk pooled from a plurality of lactating HIV-infected females.

13. A method for effecting passive mucosal immunity to infection by the human immunodeficiency virus (HIV) in an animal susceptible to infection by HIV, said method comprising administering to said animal an IgA antibody composition that neutralizes HIV, wherein said IgA antibody composition consists essentially of secretory $IgA_1$ and $IgA_2$ isotypes.

14. The method, according to claim 13, wherein said IgA antibody composition is treated to remove the secretory piece prior to administration to said animal.

* * * * *